United States Patent
Yamazaki (10) Patent No.: US 12,338,120 B2
(45) Date of Patent: Jun. 24, 2025

(54) SENSOR

(71) Applicant: KABUSHIKI KAISHA TOSHIBA, Tokyo (JP)

(72) Inventor: Hiroaki Yamazaki, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 808 days.

(21) Appl. No.: 17/668,166

(22) Filed: Feb. 9, 2022

(65) Prior Publication Data

US 2022/0396471 A1 Dec. 15, 2022

(30) Foreign Application Priority Data

Jun. 9, 2021 (JP) ................. 2021-096291

(51) Int. Cl.
*B81B 3/00* (2006.01)

(52) U.S. Cl.
CPC ........ *B81B 3/0086* (2013.01); *B81B 2203/03* (2013.01); *B81B 2203/04* (2013.01); *B81B 2207/07* (2013.01)

(58) Field of Classification Search
CPC ............. G01N 27/128; G01N 33/0049; G01N 33/0047; G01N 33/004; G01N 33/005; G01N 27/18; B81B 3/0086; B81B 3/0045; B81B 3/0021; B81B 3/0043; B81B 3/0072; B81B 3/0078; B81B 7/0077; B81B 7/0051; B81B 7/0061; B81B 7/02;

(Continued)

(56) References Cited

U.S. PATENT DOCUMENTS

| 5,551,283 | A | 9/1996 | Manaka et al. |
| 2011/0271759 | A1* | 11/2011 | Sakai ................. G01C 19/5747 73/504.12 |
| 2013/0234263 | A1* | 9/2013 | Ikehashi ............... G01L 9/0044 257/415 |
| 2013/0283909 | A1* | 10/2013 | Furuhata ............ G01C 19/5747 73/504.12 |

(Continued)

FOREIGN PATENT DOCUMENTS

| EP | 3 534 154 A1 | 9/2019 |
| JP | H7-55748 A | 3/1995 |

(Continued)

*Primary Examiner* — Mouloucoulaye Inoussa
(74) *Attorney, Agent, or Firm* — Finnegan, Henderson, Farabow, Garrett & Dunner, LLP (57) ABSTRACT

According to one embodiment, a sensor includes a base, first and second detection element portions, first to third resistor terminals, and first and second conductive terminals. The base includes first and second base regions. The first detection element portion is provided at the first base region. The first detection element portion includes a first detection dement. The first detection dement includes a first resistance member and a first conductive member. The first resistance member includes a first resistance portion and other portion. The first conductive member includes a first conductive portion and other portion. The second detection element portion is provided at the second base region. The second detection dement portion includes a second detection element. The second detection element includes a second resistance member and a second conductive member. The second resistance member includes a second resistance portion and other portion. The second conductive member includes a second conductive portion and other portion.

20 Claims, 7 Drawing Sheets

(58) Field of Classification Search
CPC ............ B81B 2207/07; B81B 2203/03; B81B 2203/04; B81B 2201/033; B81B 2201/042; B81B 2203/0154; B81B 2203/0136; B81B 2203/0127; B81B 2201/0264; B81B 2203/0163; B81B 2207/012; B81B 2203/053; B81B 2201/0292; B81B 2201/0228; B81B 2201/0235; H04R 19/005; G01J 3/45; G01J 3/06; G01J 3/4535; G01J 3/021; G01J 3/0202; G02B 26/06; G02B 26/0841; G02B 26/105; G02B 26/085; G02B 26/10; G02B 27/0176; H02N 1/008; G01P 15/125; G01P 15/0802; G01P 2015/0862; G01P 2015/0828; G01L 1/148; G01L 5/228; G01L 5/165; G01L 9/0072; G01L 1/142; G01L 1/144; G01L 9/12; B25J 13/082; B25J 13/084; G06F 3/016; Y10T 74/10; B81C 1/0023; B81C 1/00269; B81C 1/00166; B81C 2203/0785; B81C 2203/0792; B81C 2203/0109

See application file for complete search history.

(56) References Cited

U.S. PATENT DOCUMENTS

| | | | |
|---|---|---|---|
| 2014/0245831 A1* | 9/2014 | Furuhata | G01C 19/574 73/504.12 |
| 2015/0362317 A1* | 12/2015 | Furuhata | G01C 19/5747 73/504.12 |
| 2018/0292338 A1 | 10/2018 | Liu et al. | |
| 2019/0086377 A1* | 3/2019 | Ikehashi | G01N 27/221 |
| 2019/0330053 A1* | 10/2019 | Tseng | B81B 7/0077 |
| 2020/0080954 A1* | 3/2020 | Yamazaki | G01N 27/123 |
| 2020/0088519 A1* | 3/2020 | Jomori | G01C 19/5762 |
| 2021/0109071 A1* | 4/2021 | Hayashi | G01N 33/0073 |
| 2021/0175035 A1* | 6/2021 | Yamazaki | H01H 59/0009 |
| 2022/0107285 A1* | 4/2022 | Tanabe | G01N 27/18 |

FOREIGN PATENT DOCUMENTS

| | | |
|---|---|---|
| JP | 2010-197285 A | 9/2010 |
| JP | 2019-152451 A | 9/2019 |
| JP | 2020-41893 A | 3/2020 |
| JP | 6797852 B2 | 12/2020 |
| JP | 6926040 B2 | 8/2021 |

* cited by examiner

SENSOR

CROSS-REFERENCE TO RELATED APPLICATIONS

This application is based upon and claims the benefit of priority from Japanese Patent Application No. 2021-096291, filed on Jun. 9, 2021; the entire contents of which are incorporated herein by reference.

FIELD

Embodiments described herein relate generally to a sensor.

BACKGROUND

For example, there is a sensor that uses a MEMS (Micro Electro Mechanical Systems) element or the like. It is desirable to improve the characteristics of the sensor.

DETAILED DESCRIPTION

According to one embodiment, a sensor includes a base, a first detection element portion, a second detection element portion, a first resistor terminal, a second resistor terminal, a third resistor terminal, a first conductive terminal, and a second conductive terminal. The base includes a first base region and a second base region. The first detection element portion is provided at the first base region. The first detection element portion includes a first detection element. The first detection element includes a first resistance member and a first conductive member. The first resistance member includes a first resistance portion and a first resistance other portion. The first conductive member includes a first conductive portion and a first conductive other portion. The second detection element portion is provided at the second base region. The second detection element portion includes a second detection element. The second detection element includes a second resistance member and a second conductive member. The second resistance member includes a second resistance portion and a second resistance other portion. The second conductive member includes a second conductive portion and a second conductive other portion. The first resistor terminal is electrically connected with the first resistance portion. The second resistor terminal is electrically connected with the first resistance other portion and the second resistance portion. The third resistor terminal is electrically connected with the second resistance other portion. The first conductive terminal is electrically connected with the first conductive portion. The second conductive terminal is electrically connected with the first conductive other portion.

According to one embodiment, a sensor includes a base, a first detection element portion, a second detection element portion, a first resistor terminal, a second resistor terminal, a third resistor terminal, a fourth resistor terminal, a first conductive terminal, and a second conductive terminal. The base includes a first base region and a second base region. The first detection element portion is provided at the first base region. The first detection element portion includes a first detection element. The first detection element includes a first resistance member and a first conductive member. The first resistance member includes a first resistance portion and a first resistance other portion. The first conductive member includes a first conductive portion and a first conductive other portion. The second detection element portion is provided at the second base region. The second detection element portion includes a second detection element. The second detection element includes a second resistance member and a second conductive member. The second resistance member includes a second resistance portion and a second resistance other portion. The second conductive member includes a second conductive portion and a second conductive other portion. The first resistor terminal is electrically connected with the first resistance portion. The second resistor terminal is electrically connected with the first resistance other portion. The third resistor terminal is electrically connected with the second resistance other portion. The fourth resistor terminal is electrically connected with the second resistance portion. The first conductive terminal is electrically connected with the first conductive portion. The second conductive terminal is electrically connected with the first conductive other portion.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1:
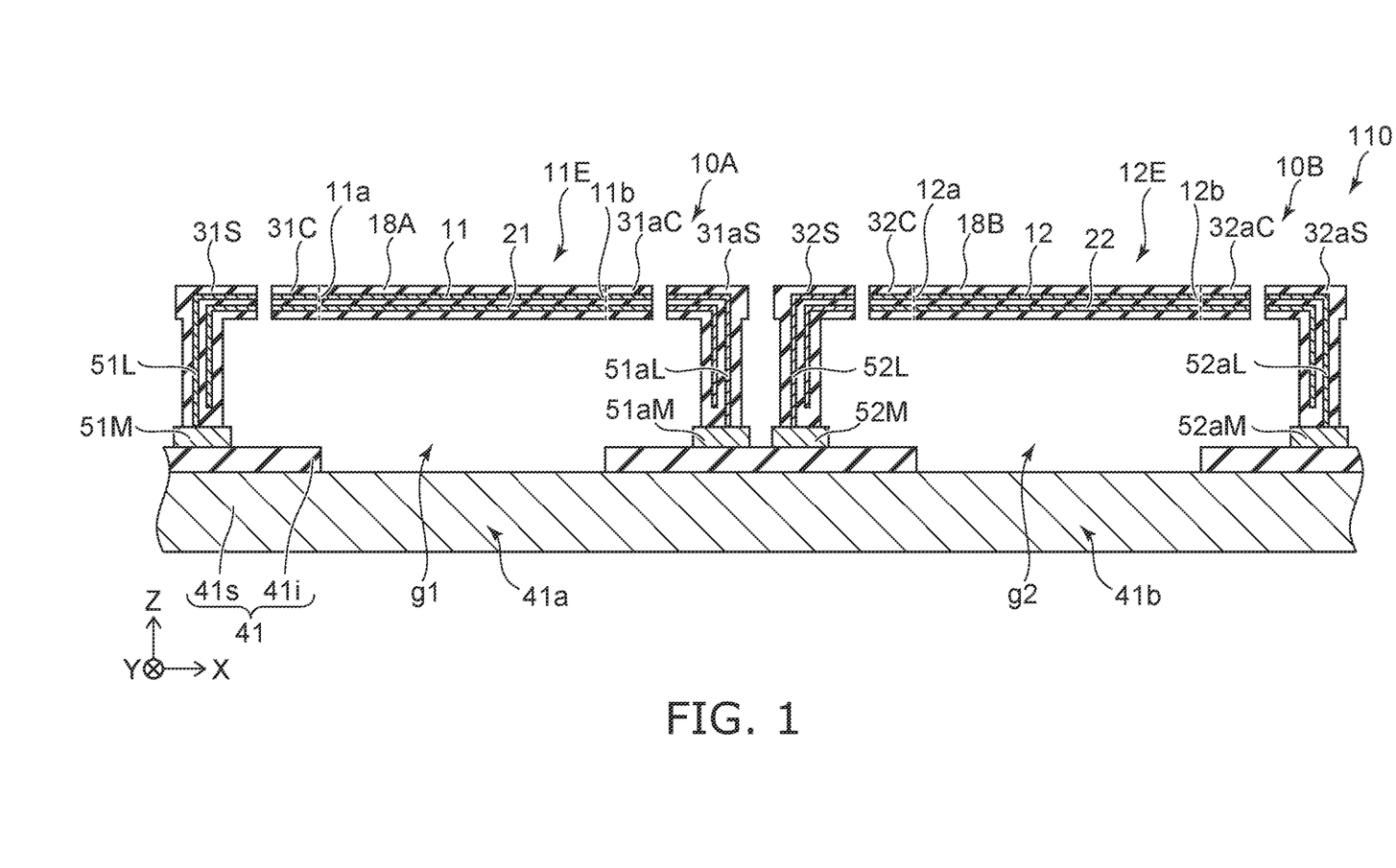
FIG. 1 is a schematic cross-sectional view illustrating a sensor according to a first embodiment.

FIG. 1 is a schematic cross-sectional view illustrating a sensor according to a first embodiment.

Figure 2A:
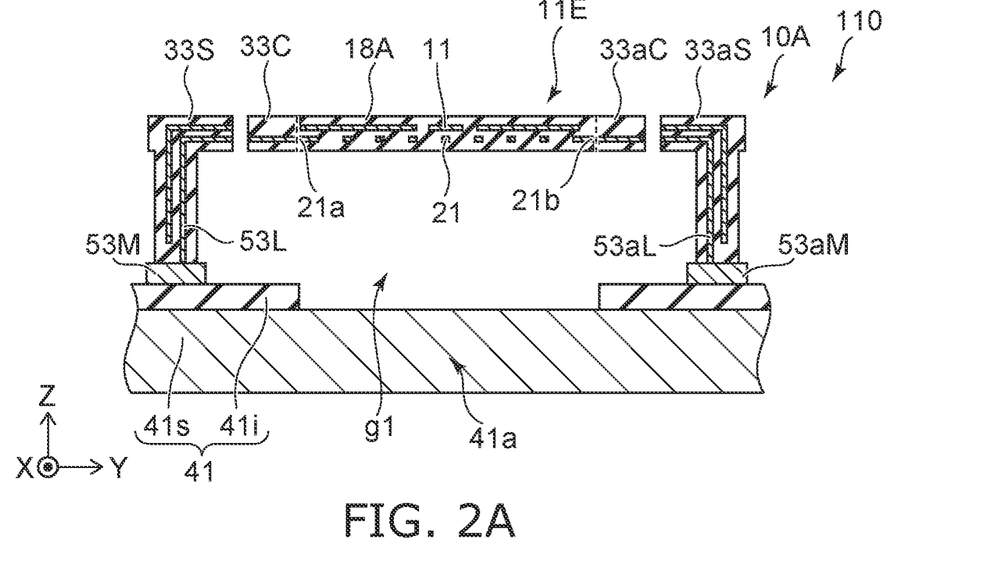
FIG. 2A and FIG. 2B are schematic cross-sectional views illustrating the sensor according to the first embodiment.
Figure 2B:
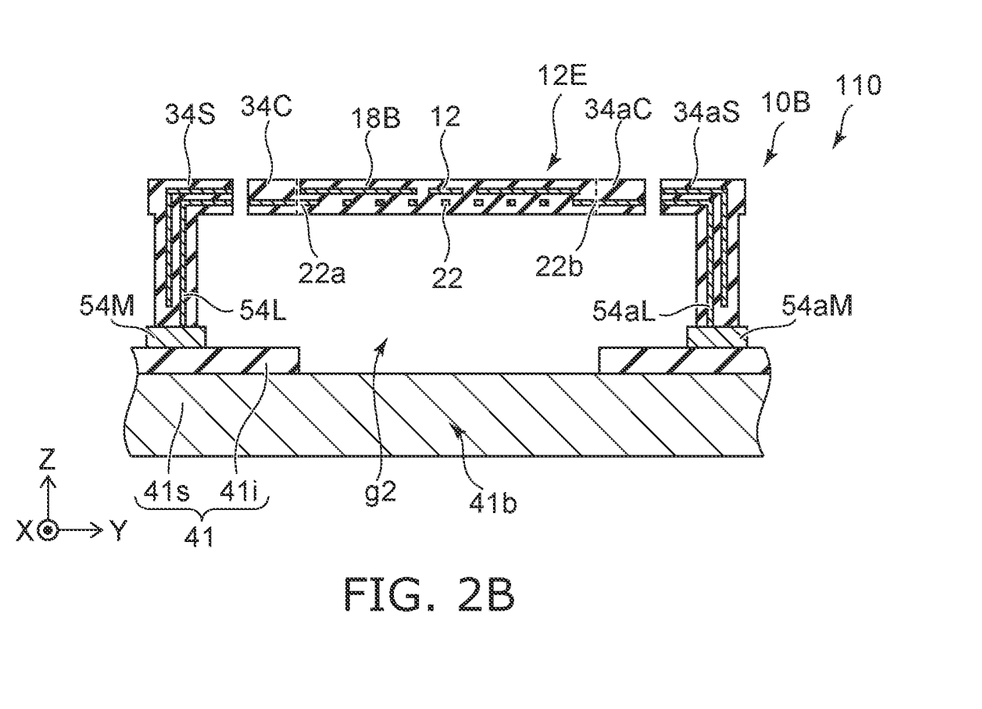

FIG. 2A and FIG. 2B are schematic cross-sectional views illustrating the sensor according to the first embodiment.

Figure 3:
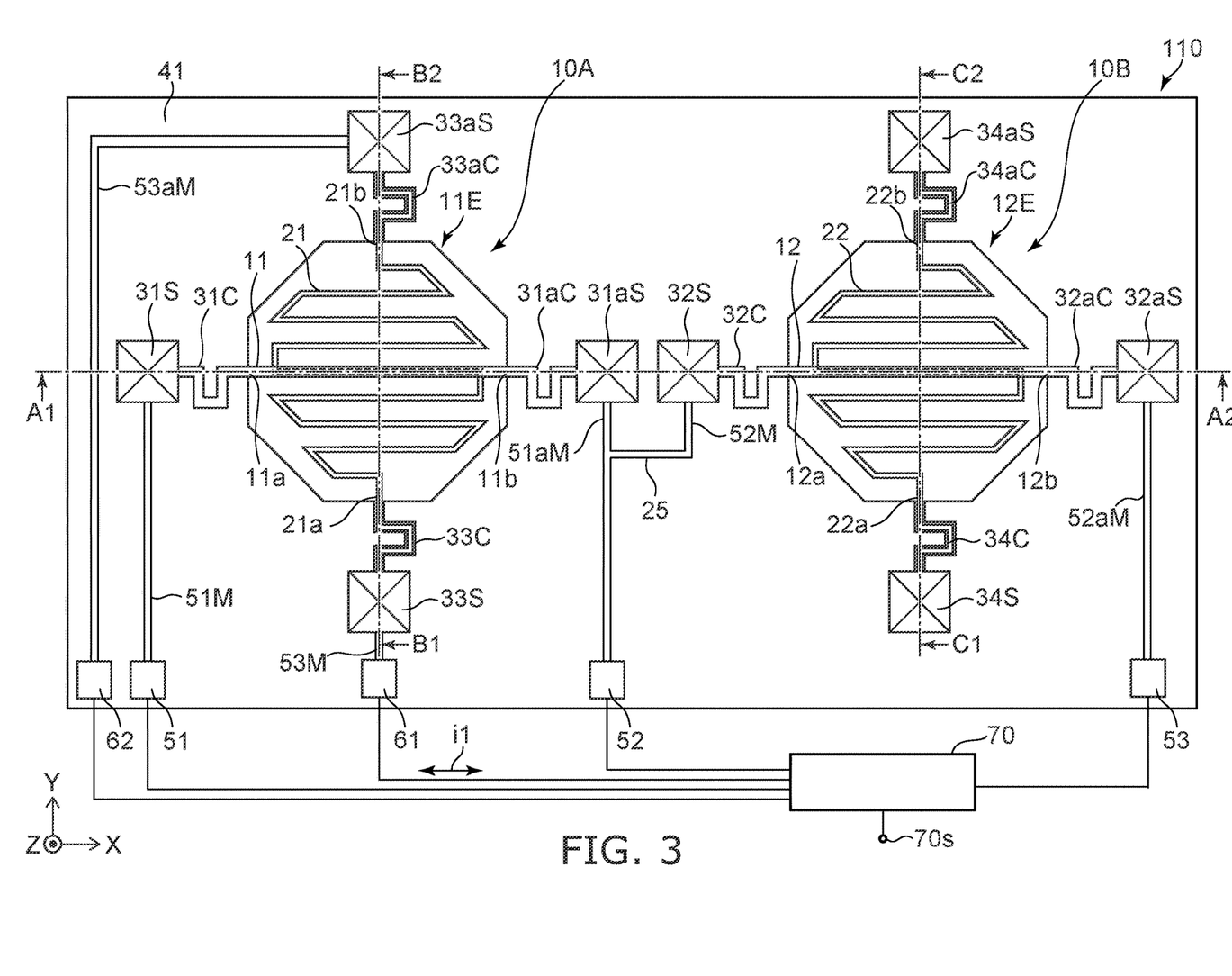
FIG. 3 is a schematic plan view illustrating the sensor according to the first embodiment.

FIG. 3 is a schematic plan view illustrating the sensor according to the first embodiment, FIG. 1 is a cross-sectional view taken along the line A1-A2 of FIG. 3. FIG. 2A is a cross-sectional view taken along the line B1-B2 of FIG. 3. FIG. 2B is a cross-sectional view taken along the line C1-C2 of FIG. 3.

As shown in FIGS. 1, 2A, 2B and 3, a sensor 110 according to the embodiment includes a base 41, a first detection element portion 10A, a second detection element portion 10B, a first resistor terminal 51, a second resistor terminal 52, a third resistor terminal 53, a first conductive terminal 61, and a second conductive terminal 62.

The base 41 includes a first base region 41a and a second base region 41b. In this example, the base 41 includes a substrate 41s and an insulating film 41i. The substrate 41s may be, for example, a semiconductor substrate (for example, a silicon substrate), The substrate 41s may include, for example, a semiconductor circuit or the like. The substrate 41s may include a connecting member such as a via electrode.

The first detection element portion 10A is provided at the first base region 41a. A direction from the first base region 41a to the first detection element portion 10A is a Z-axis direction. One direction perpendicular to the Z-axis direction is defined as an X-axis direction. The direction perpendicular to the Z-axis direction and the X-axis direction is defined as a Y-axis direction.

The first detection element portion 10A includes a first detection element 11E, The first detection element 11E includes a first resistance member 11 and a first conductive member 21. As shown in FIGS. 1 and 3, the first resistance member 11 includes a first resistance portion 11a and a first resistance other portion 11b. For example, the first resistance portion 11a may be one end of the first resistance member 11, The first resistance other portion 11b may be another end portion of the first resistance member 11. As shown in FIGS. 2A and 3, the first conductive member 21 includes a first conductive portion 21a and a first conductive other portion 21b. For example, the first conductive portion 21a may be one end of the first conductive member 21. The first conductive other portion 21b may be another end of the first conductive member 21.

As shown in FIGS. 1 and 3, in this example, the first detection element portion 10A further includes a first connection portion 31C and a first support portion 31S. The first support portion 31S is fixed to the base 41. A part of the first connection portion 31C is supported by the first support portion 31S, Another part of the first connection portion 31C supports the first detection element 11E to be apart from the first base region 41a. A first gap g1 is provided between the first base region 41a and the first detection element 11E.

In this example, the first detection element portion 10A further includes a first other connection portion 31aC and a first other support portion 31aS. The first other support portion 31aS is fixed to the base 41. A part of the first other connection portion 31aC is supported by the first other support portion 31aS. Another part of the first other connection portion 31aC supports the first detection element 11E to be apart from the first base region 41a. In this example, at least a part of the first detection element 11E is located between the first connection portion 31C and the first other connection portion 31aC.

The second detection element portion 103 is provided at the second base region 41b. A direction from the second base region 41b to the second detection element portion 10B is along the Z-axis direction.

The second detection element portion 103 includes a second detection element 12E. The second detection element 12E includes a second resistance member 12 and a second conductive member 22. As shown in FIGS. 1 and 3, the second resistance member 12 includes a second resistance portion 12a and a second resistance other portion 12b. For example, the second resistance portion 12a may be one end of the second resistance member 12. The second resistance other portion 12b may be another end portion of the second resistance member 12, As shown in FIGS. 2B and 3, the second conductive member 22 includes a second conductive portion 22a and a second conductive other portion 22b. For example, the second conductive portion 22a may be one end of the second conductive member 22. The second conductive other portion 22b may be another end of the second conductive member 22.

As shown in FIGS. 1 and 3, in this example, the second detection element portion 10B further includes a second connection portion 32C and a second support portion 32S. The second support portion 32S is fixed to the base 41, A part of the second connection portion 32C is supported by the second support portion 32S. Another part of the second connection portion 32C supports the second detection element 12E to be apart from the second base region 41b. A second gap g2 is provided between the second base region 41b and the second detection element 12E.

In this example, the second detection element portion 10B further includes a second other connection portion 32aC and a second other support portion 32aS. The second other support portion 32aS is fixed to the base 41. A part of the second other connection portion 32aC is supported by the second other support portion 32aS, Another part of the second other connection portion 32aC supports the second detection element 12E to be apart from the second base region 41b. In this example, at least a part of the second detection element 12E is between the second connection portion 32C and the second other connection portion 32aC.

By supporting the first detection element 11E and the second detection element 12E apart from the base 41, it is possible to suppress the heat of these detection elements from being conducted through the base 41, This facilitates stable detection of the detection target with high sensitivity.

The first resistor terminal 51 is electrically connected with the first resistance portion 11a. In this example, the second resistor terminal 52 is electrically connected with the first resistance other portion lib and the second resistance portion 12a. The third resistor terminal 53 is electrically connected with the second resistor other portion 12b. As will be described later, other resistor terminals may be provided. In this case, the second resistor terminal 52 may be electrically connected with the first resistance other portion lib, and the other resistor terminal may be electrically connected with the second resistance portion 12a.

In this example, as shown in FIG. 3, the connecting conductive member 25 is provided. The connecting conductive member 25 is provided on the base 41, The connecting conductive member 25 electrically connects the first resistance other portion 11b and the second resistance portion 12a. In this example, the second resistor terminal 52 is electrically connected with the first resistance other portion lib and the second resistance portion 12a via the connecting conductive member 25.

The first conductive terminal 61 is electrically connected with the first conductive portion 21a, The second conductive terminal 62 is electrically connected with the first conductive other portion 21b.

As shown in FIG. 3, a processor 70 may be provided in the sensor 110. The processor 70 may be included in the sensor 110. The processor 70 may be provided separately from the sensor 110, The processor 70 is electrically connected with the first resistor terminal 51, the second resistor terminal 52, the third resistor terminal 53, the first conductive terminal 61, and the second conductive terminal 62.

The processor 70 can perform a first operation. In the first operation, the processor 70 supplies the first current i1 between the first conductive terminal 61 and the second conductive terminal 62 to raise the temperature of the first detection element 11E, A first current i1 flows through the first conductive member 21. Due to Joule heat, the temperature of the first conductive member 21 rises with respect to the atmospheric temperature, and the temperature of the first detection element 11E rises. The first current i1 may be alternating current or direct current.

In the first operation, the processor 70 can output a signal 70s corresponding to a first ratio of a first electric resistance between a first resistor terminal 51 and the second resistor terminal 52 to a second electric resistance between the second resistor terminal 52 and the third resistor terminal 53. "Corresponding to the first ratio" includes "corresponding to the reciprocal of the first ratio".

For example, the electric resistance of the first resistance member 11 changes according to the temperature of the first resistance member 11. The temperature of the first resistance member 11 is substantially the same as the temperature of the first detection element 11E. For example, the electric resistance of the second resistance member 12 changes according to the temperature of the second resistance member 12. The temperature of the second resistance member 12 is substantially the same as the temperature of the second detection element 12E. As described above, in the first operation, for example, the temperature of the first detection element 11E rises, and the temperature of the first resistance member 11 also rises. On the other hand, the processor 70 does not supply a current to the second conductive member 22 in, for example, the first operation. In the first operation, no current flows through the second conductive member 22, and the temperatures of the second detection element 12E and the second resistance member 12 do not substantially change. The first resistance member 11 and the second resistance member 12 become, for example, at least a part of a half-bridge circuit. The first ratio of the first electric resistance to the second electric resistance depends on the temperature difference between the two resistance members.

Here, the first ratio when a first element to be inspected exists in the atmosphere around the first detection element 11E changes from the first ratio when the atmosphere does not include the first element. This is based on the fact that the temperature conduction characteristics of the first detection element 11E change depending on the presence (and concentration) of the first element. For example, the first element includes at least one selected from the group consisting of hydrogen, helium, carbon dioxide, methane and sulfur hexafluoride (SF6). When the atmosphere includes hydrogen as the first element, the temperature of the first detection element 11E is lower than when the atmosphere includes substantially no hydrogen. The first ratio changes according to the concentration of the first element included in the atmosphere around the first detection element and the second detection element.

By utilizing such characteristics, the sensor 110 can detect the first element. The first ratio changes according to the concentration of the first element included in the atmosphere around the first detection element 11E and the second detection element 12E, For example, the first electric resistance when the temperature of the first detection element 11E rises changes according to the concentration of the first element included in the atmosphere around the first detection element 11E, For example, the processor 70 can detect the presence/absence or concentration of the first element to be detected by detecting the first ratio.

In the embodiment, a plurality of detection element portions are provided on one base 41. The second detection element portion 103E has substantially the same structure as the first detection element portion 10A. As a result, the heat capacity of the second detection element portion 10B becomes the same as the heat capacity of the first detection element portion 10A. In the embodiment, by detecting the ratio of the electric resistances of these two detection element portions, it is possible to detect with higher accuracy and higher sensitivity.

For example, even when the ambient temperature of the sensor 110 changes, the influence of the change in the ambient temperature can be suppressed by using the two detection element portions. In the embodiment, the change in the electric resistance of the first detecting element 11E due to the presence or absence or the concentration of the first element is detected by suppressing other influences. It is possible to provide a sensor whose characteristics can be improved.

In the embodiment, the second detection element portion 10B has substantially the same structure as the first detection element portion 10A. The length, width, thickness and material of the second resistance member 12 are substantially the same as the length, width, thickness and material of the first resistance member 11. The length, width, thickness and material of the second conductive member 22 are substantially the same as the length, width, thickness and material of the first conductive member 21.

In the embodiment, the second conductive member 22 does not have to be supplied with an electric current. For example, at least one of the second conductive portion 22a and the second conductive other portion 22b may have a floating potential. For example, the second conductive member 22 is a dummy conductive member. The potential of the second conductive member 22 may be a fixed potential (for example, a ground potential).

As shown in FIG. 1, the first detection element portion 10A (and the first detection element 11E) may include the first insulating portion 18A. The second detection element portion 10B (and the second detection element 12E) may include the second insulating portion 18B, At least a part of the first insulating portion 18A is provided around the first resistance member 11 and the first conductive member 21. A part of the first insulating portion 18A is provided between the first resistance member 11 and the first conductive member 21. At least a part of the second insulating portion 18B is provided around the second resistance member 12 and the second conductive member 22. A part of the second insulating portion 18B is provided between the second resistance member 12 and the second conductive member 22. The second insulating portion 18B has substantially the same structure as the first insulating portion 18A. The length, width, thickness and material of the second insulating portion 188 are substantially the same as the length, width, thickness and material of the first insulating portion 18A.

For example, the thermal conductivity of hydrogen gas is 174 mW (m·K). The thermal conductivity of carbon dioxide is 14.2 mW (m·K). The thermal conductivity of nitrogen is 24.3 mW (m·K), The thermal conductivity of methane is 30 mW/(m·K). For example, when hydrogen is included in the air atmosphere, the change in the temperature of the first resistance member 11 is greater than the change in the temperature of the second resistance member 12, due to the change in the effective thermal conductivity of the atmosphere according to the presence or absence or concentration of hydrogen. Higher sensitivity detection can be performed when the first element includes hydrogen. The sensor 110 is, for example, a thermal conductivity-type hydrogen sensor.

As shown in FIG. 1, the first detection element portion 10A may further include a first conductive layer 51L, The first conductive layer 51L is electrically connected with the first resistance portion 11a of the first resistance member 11. At least a part of the first conductive layer 51L may be provided at the first support portion 31S. In this example, the first conductive layer 51L is electrically connected with the wiring layer 51M provided on the base 41. The wiring layer 51M is electrically connected with the first resistor terminal 51 (see FIG. 3).

As shown in FIG. 1, the second detection element portion 103E may further include a second conductive layer 52L. The second conductive layer 52L is electrically connected with the second resistance portion 12a of the second resistance member 12. At least a part of the second conductive layer 52L may be provided at the second support portion 32S. In this example, the second conductive layer 52L is electrically connected with the wiring layer 52M provided on the base 41. The wiring layer 52M is electrically connected with the second resistor terminal 52 (see FIG. 3).

A current flowing between the first resistor terminal 51 and the first resistance portion 11a flows through the first conductive layer 51L. A current flowing between the second resistor terminal 52 and the second resistance portion 12a flows through the second conductive layer 52L.

The first detection element portion 10A may further include a first other conductive layer 51aL. The first other conductive layer 51aL is electrically connected with the first resistance other portion lib of the first resistance member 11. At least a part of the first other conductive layer 51aL may be provided at the first other support portion 31aS. In this example, the first other conductive layer 51aL is electrically connected with the wiring layer 51aM provided on the base 41. The wiring layer 51aM is electrically connected with the second resistor terminal 52 (see FIG. 3).

The second detection element portion 10B may further include a second other conductive layer 52aL. The second other conductive layer 52aL is electrically connected with the second resistance other portion 12b of the second resistance member 12. At least a part of the second other conductive layer 52aL may be provided at the second other support portion 32aS. In this example, the second other conductive layer 52aL is electrically connected with the wiring layer 52aM provided on the base 41. The wiring layer 52aM is electrically connected with the third resistor terminal 53 (see FIG. 3).

As shown in FIGS. 2A and 3, in this example, the first detection element portion 10A includes a third connection portion 33C and a third support portion 33S. The third support portion 33S is fixed to the base 41. A part of the third connection portion 33C is supported by the third support portion 33S. Another part of the third connection portion 33C supports the first detection element 11E to be apart from the first base region 41a.

In this example, the first detection element portion 10A includes a third other connection portion 33aC and a third other support portion 33aS. The third other support portion 33aS is fixed to the base 41. A part of the third other connection portion 33aC is supported by the third other support portion 33aS. Another part of the third other connection portion 33aC supports the first detection element 11E to be apart from the first base region 41a.

As shown in FIG. 2A, the first detection element portion 10A may further include a third conductive layer 53L. At least a part of the third conductive layer 53L is provided at the third support portion 33S. In this example, the third conductive layer 53L is electrically connected with the wiring layer 53M provided on the base 41. The wiring layer 53M is electrically connected with the first conductive terminal 61 (see FIG. 3). The first current i1 flowing between the first conductive terminal 61 and the first conductive portion 21a flows through the third conductive layer 53L.

As shown in FIG. 2A, the first detection element portion 10A may further include a third other conductive layer 53aL. At least a part of the third other conductive layer 53aL is provided at the third other support portion 33a5. In this example, the third other conductive layer 53aL is electrically connected with the wiring layer 53aM provided on the base 41. The wiring layer 53aM is electrically connected with the second conductive terminal 62 (see FIG. 3), The first current i1 flowing between the second conductive terminal 62 and the first conductive other portion 21b flows through the third other conductive layer 53aL.

As shown in FIGS. 2B and 3, in this example, the second detection element portion 10B includes a fourth connection portion 34C and a fourth support portion 34S. The fourth support portion 34S is fixed to the base 41. A part of the fourth connection portion 34C is supported by the fourth support portion 34S. Another part of the fourth connection portion 34C supports the second detection element 12E to be apart from the second base region 41b.

In this example, the second detection element portion 10B includes a fourth other connection portion 34aC and a fourth other support portion 34aS. The fourth other support portion 34aS is fixed to the base 41, A part of the fourth other connection portion 34aC is supported by the fourth other support portion 34aS. Another part of the fourth other connection portion 34aC supports the second detection element 12E to be apart from the second base region 41b.

As shown in FIG. 2B, the second detection element portion 10B may further include a fourth conductive layer 54L. At least a part of the fourth conductive layer 54L is provided at the fourth support portion 34S. In this example, the fourth conductive layer 54L is electrically connected with the wiring layer 54M provided on the base 41. The fourth conductive layer 54L is electrically connected with the second conductive portion 22a.

As shown in FIG. 2B, the second detection element portion 10B may further include a fourth other conductive layer 54aL. At least a part of the fourth other conductive layer 54aL is provided at the fourth other support portion 34aS. In this example, the fourth other conductive layer 54aL is electrically connected with the wiring layer 54aM provided on the base 41. The fourth other conductive layer 54aL is electrically connected with the second conductive other portion 22b, FIG. 4A and FIG. 4B are schematic plan views illustrating the sensor according to the first embodiment.

These figures are plan views of the layer including the first resistance member 11 and the second resistance member 12.

Figure 4A:
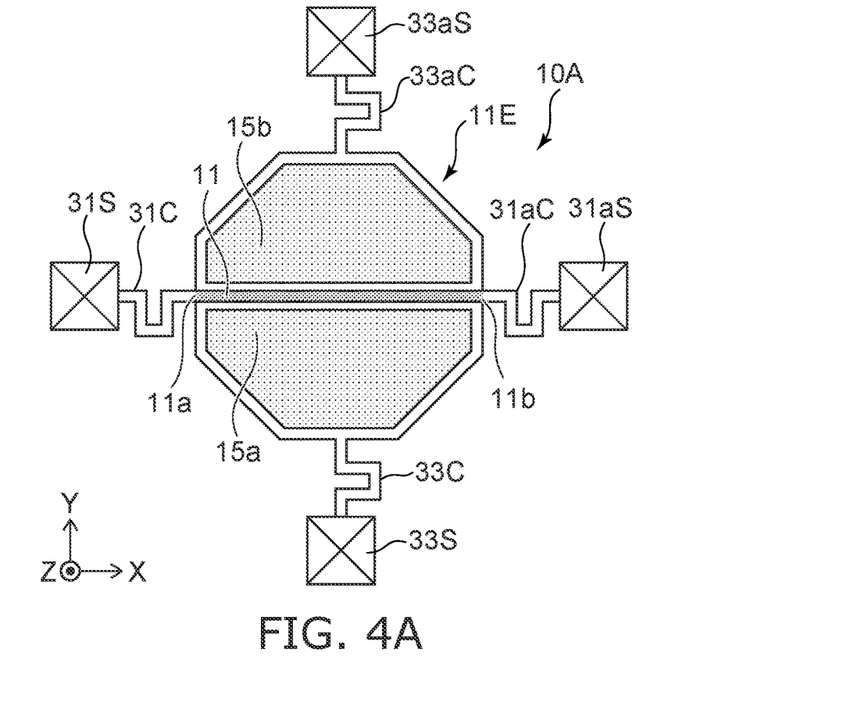
FIG. 4A and FIG. 4B are schematic plan views illustrating the sensor according to the first embodiment.

As shown in FIG. 4A, the first detection dement 11E may include a first layer 15a and a second layer 15b, The first layer 15a and the second layer 15b have the same material and thickness as the first resistance member 11. The first resistance member 11 is provided between the first layer 15a and the second layer 15b. By providing these layers, the warp (deformation) of the first detection dement 11E is suppressed.

Figure 4B:
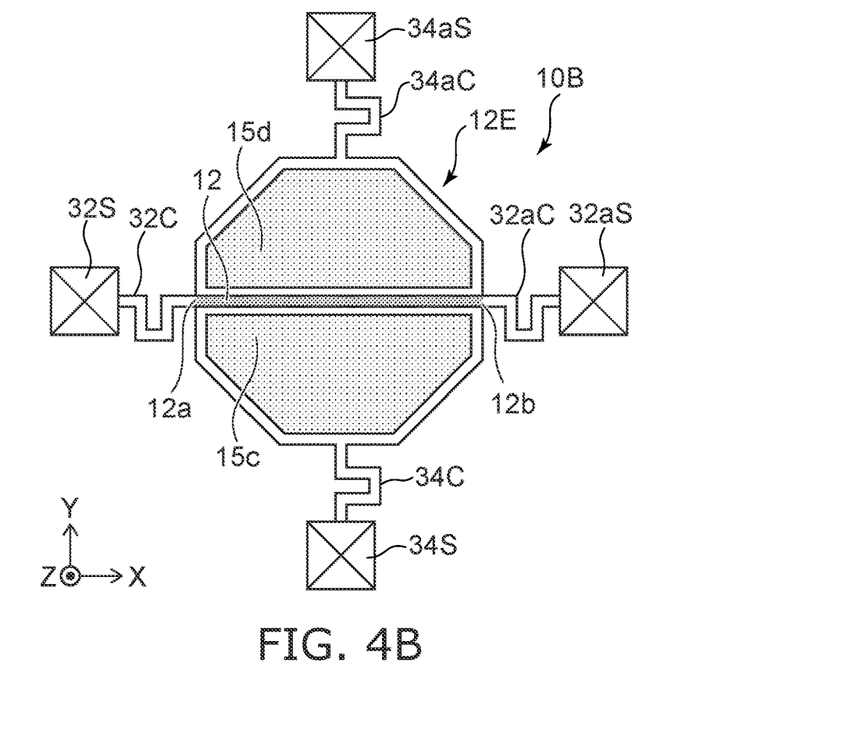

As shown in FIG. 4B, the second detection dement 12E may include a third layer 15c and a fourth layer 15d. The third layer 15c and the fourth layer 15d have the same material and thickness as the second resistance member 12. The second resistance member 12 is provided between the third layer 15c and the fourth layer 15d, By providing these layers, the warp (deformation) of the second detection dement 12E is suppressed, FIG. 5 is a schematic plan view illustrating a sensor according to the first embodiment.

Figure 5:
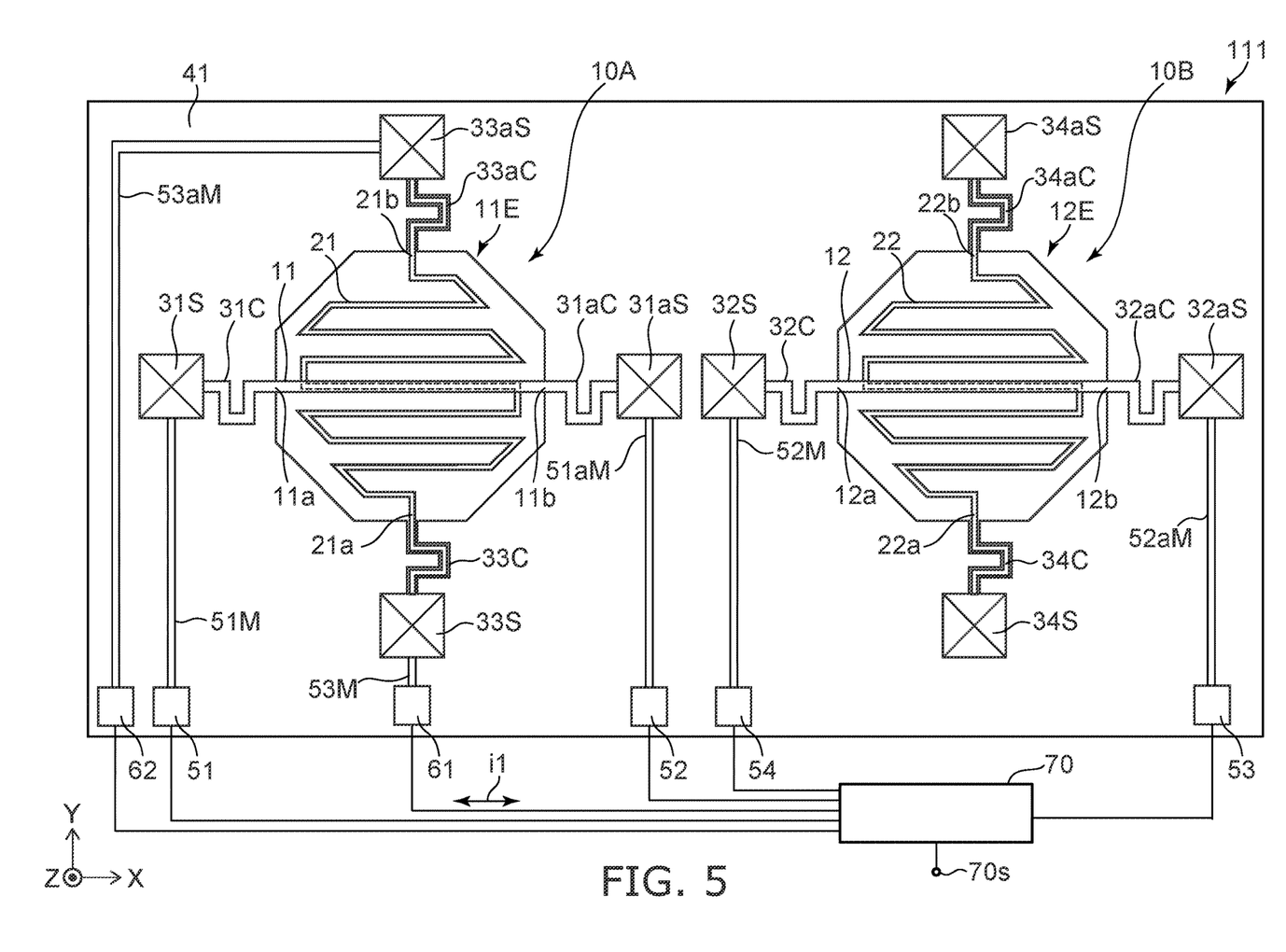
FIG. 5 is a schematic plan view illustrating a sensor according to the first embodiment.

As shown in FIG. 5, in a sensor 111 according to the embodiment, a fourth resistor terminal 54 is provided in addition to the first resistor terminal 51, the second resistor terminal 52, the third resistor terminal 53, the first conductive terminal 61, and the second conductive terminal 62, the first resistor terminal 51, the second resistor terminal 52, the third resistor terminal 53, and the second conductive terminal 62. Other configurations of the sensor 111 may be the same as those of the sensor 110.

In the sensor 111, the first resistor terminal 51 is electrically connected with the first resistance portion 11a. The second resistor terminal 52 is electrically connected with the first resistor other portion 11b. The third resistor terminal 53 is electrically connected with the second resistor other portion 12b. The fourth resistor terminal 54 is electrically connected with the second resistance portion 12a. The first conductive terminal 61 is electrically connected with the first conductive portion 21a. The second conductive terminal 62 is electrically connected with the first conductive other portion 21b.

In this case as well, the processor 70 may be provided. The processor 70 is electrically connected with the first resistor terminal 51, the second resistor terminal 52, the third resistor terminal 53, the fourth resistor terminal 54, the first conductive terminal 61, and the second conductive terminal 62, The processor 70 can perform the first operation. In the first operation, the processor 70 supplies the first current i1 between the first conductive terminal 61 and the second conductive terminal 62 to raise the temperature of the first detection element 11E. In the first operation, the processor 70 can output the signal 70s corresponding to the first ratio of the first electric resistance between the first resistor terminal 51 and the second resistor terminal 52 to the second electric resistance between the third resistor terminal 53 and the fourth resistor terminal 54, For example, the operation in the sensor 111 other than the above may be the same as the operation in the sensor 110.

The sensor 111 can also detect changes in the electric resistance of the first detection element 11E due to the presence or absence or concentration of the first element while suppressing other effects. It is possible to provide a sensor whose characteristics can be improved.

In the sensor 110 and the sensor 111, for example, the configuration (shape, material, etc.) of the first detection element 11E may be substantially the same as the configuration (shape, material, etc.) of the second detection element 12E. In this case, in these detection elements, the difference in temperature rise due to the difference in configuration does not substantially occur. Higher accuracy detection can be performed more easily. For example, when the processor 70 obtains the signal 70s, the processor 70 supplies a detection current to, for example, the first detection element 11E and the second detection element 12E. The detection current flows through the first resistance member 11 and the second resistance member 12. The temperature rise due to Joule heat generated by the detection current is substantially the same between the first detection element 11E and the second detection element 12E.

Second Embodiment

Figure 6:
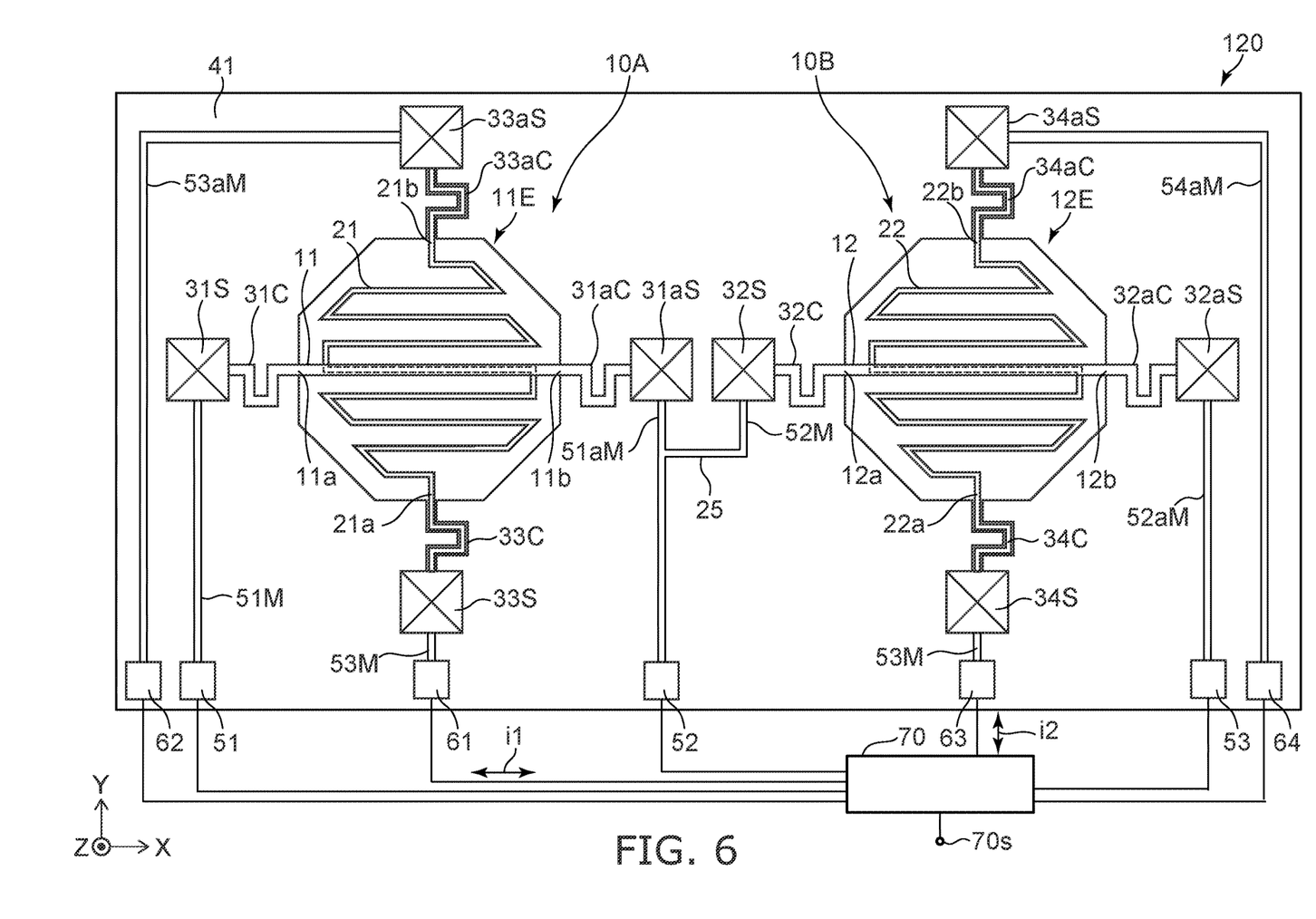
FIG. 6 is a schematic plan view illustrating a sensor according to a second embodiment.

FIG. 6 is a schematic plan view illustrating a sensor according to a second embodiment.

As shown in FIG. 6, in a sensor 120 according to the embodiment, a third conductive terminals 63 and the fourth conductive terminal 64 are provided in addition to the first resistor terminal 51, the second resistor terminal 52, the third resistor terminal 53, the first conductive terminal 61, and the second conductive terminal 62, the first resistor terminal 51, the second resistor terminal 52, the third resistor terminal 53, and the second conductive terminal 62, Other configurations of the sensor 120 may be the same as those of the sensor 110.

The third conductive terminal 63 is electrically connected with the second conductive portion 22a. The fourth conductive terminal 64 is electrically connected with the second conductive other portion 22b.

The processor 70 can perform a second operation. For example, the processor 70 can switch the second operation from the first operation.

The processor 70 supplies a second current i2 between the third conductive terminal 63 and the fourth conductive terminal 64 to raise the temperature of the second detection element 12E, The second current i2 may be alternating current or direct current. In the second operation, the processor 70 can output the signal 70s corresponding to a second ratio of a third electric resistance between the first resistor terminal 51 and the second resistor terminal 52 to a fourth electric resistance between the second resistor terminal 52 and the third resistor terminal 53.

In this way, the first operation in which the first detection element 11E functions as a temperature sensor and the second operation in which the second detection element 12E functions as a temperature sensor may be switched and performed.

The processor 70 may be able to output an average of the first ratio of the first operation and the second ratio of the second operation. Higher accuracy detection is possible.

The third conductive terminal 63 and the fourth conductive terminal 64 may be provided in the sensor 111.

In the above example, the current flowing when the electric resistance of the first resistance member 11 is detected passes through the first support portion 31S and the first other support portion 31aS. At this time, the first current i1 flowing through the first conductive member 21 flows through the third support portion 33S and the third other support portion 33aS.

In the embodiment, the first current i1 flowing through the first conductive member 21 may pass through the first support portion 31S and the first other support portion 31aS.

For example, the first detection element portion 10A may include the third conductive layer 53L (see FIG. 2A). At least a part of the third conductive layer 53L is provided at the first support portion 31S, The first current i1 flowing between the first conductive terminal 61 and the first conductive portion 21a flows through the third conductive layer 53L. For example, the second detection element portion 10B may further include the fourth conductive layer 54L (see FIG. 2B). At least a part of the fourth conductive layer 54L is provided at the second support portion 32S. The fourth conductive layer 54L is electrically connected with the second conductive portion 22a. As described above, various modifications are possible in the embodiment.

Third Embodiment

Figure 7:
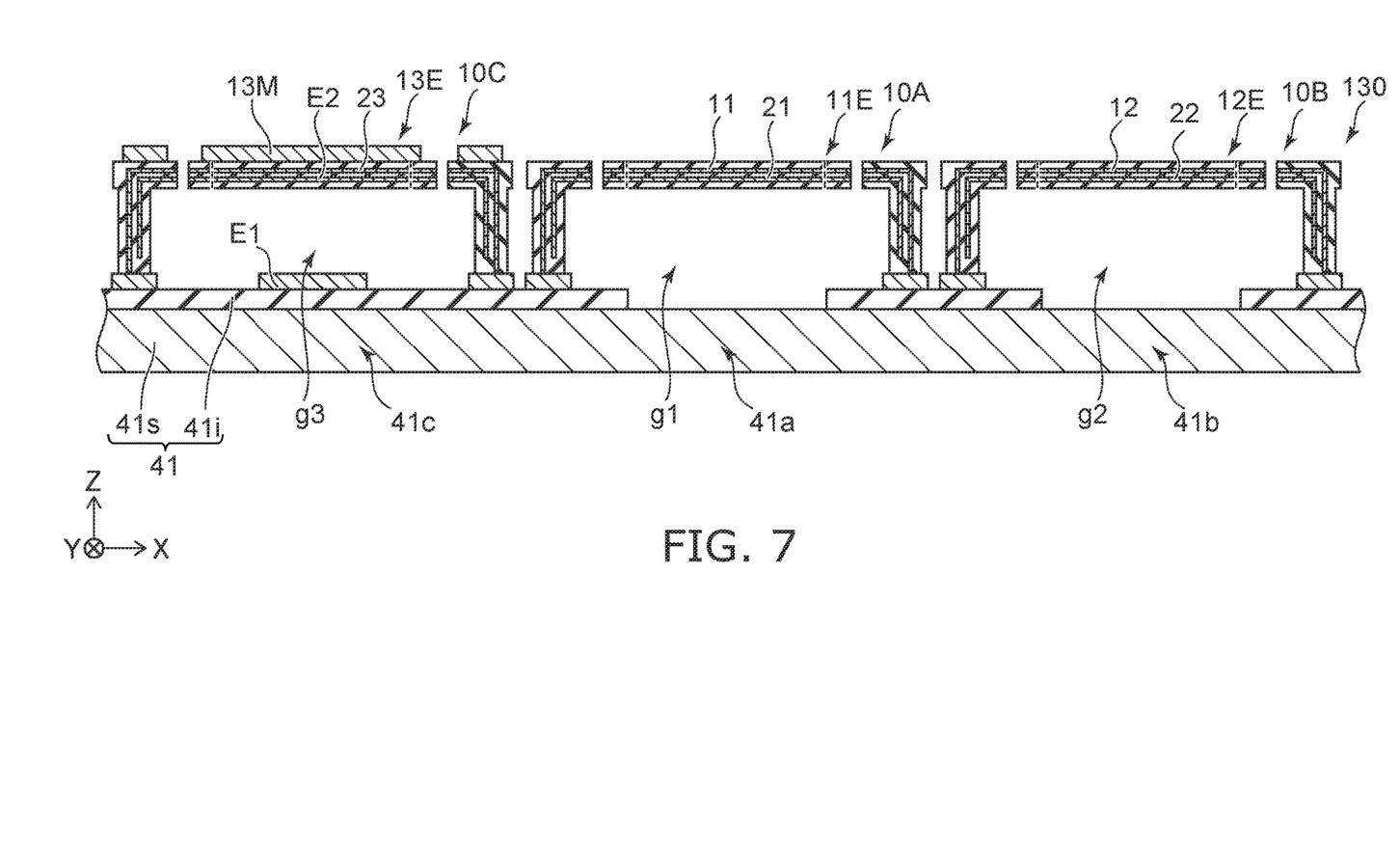
FIG. 7 is a schematic plan view illustrating a sensor according to a third embodiment.

FIG. 7 is a schematic plan view illustrating a sensor according to a third embodiment.

As shown in FIG. 7, a sensor 130 according to the embodiment includes the third detection element portion 10C. The sensor 130 includes the base 41, the first detection element portion 10A, and the second detection element portion 10B, The sensor 130 includes the first resistor terminal 51, the second resistor terminal 52, the third resistor terminal 53, the first conductive terminal 61, and the second conductive terminal 62, which have already been described.

The base 41 includes a third base region 41c. The third detection element portion 10C is provided at the third base region 41c. The third detection element portion 10C includes a third detection element 13E. The third detection element 13E includes a fixed electrode E1 and a movable electrode E. In this example, the third detection element 13E includes a member 13M and a third conductive member 23. In this example, the movable electrode E2 is provided between the fixed electrode E1 and the member 13M. A third conductive member 23 is provided between the movable electrode E2 and the member 13M.

A third gap g3 is provided between the fixed electrode E1 and the movable electrode E2. A distance between the fixed electrode E1 and the movable electrode E2 changes according to the concentration of the first element included in the environment around the third detection element 13E. This is based on the deformation of the first movable electrode E2 caused by the adsorption of the first element on the movable electrode E2 and the member 13M around the movable electrode E2, A capacitance between the fixed electrode E1 and the movable electrode E2 changes according to the deformation of the distance. The processor 70 can output a value according to a change in the electric capacitance. The third detection element portion 10C is a capacitive-type sensor.

For example, the processor 70 can supply an electric current to the third conductive member 23, This current raises the temperature of the member 13M. For example, in the member 13M, it becomes easy to efficiently take in (for example, adsorb) the first element. For example, the change in capacitance with respect to the concentration of the first element can be increased. It becomes easy to obtain high sensitivity.

In the sensor 130, any configuration described with respect to the first embodiment and the second embodiment can be applied to the first detection element portion 10A and the second detection element portion 10B.

In one example according to the embodiment, the first conductive member 21 may be provided between the base 41 (first base region 41a) and the first resistance member 11. For example, a distance along the Z-axis direction between the first base region 41a and the first conductive member 21 is shorter than a distance along the Z-axis direction between the first base region 41a and the first resistance member 11. In another example, the first resistance member 11 may be provided between the base 41 (first base region 41a) and the first conductive member 21. For example, the distance along the Z-axis direction between the first base region 41a and the first resistance member 11 is shorter than the distance along the Z-axis direction between the first base region 41a and the first conductive member 21.

In one example according to the embodiment, the second conductive member 22 may be provided between the base 41 (second base region 41b) and the second resistance member 12, For example, a distance along the Z-axis direction between the second base region 41b and the second conductive member 22 is shorter than a distance along the Z-axis direction between the second base region 41b and the second resistance member 12. In another example, the second resistance member 12 may be provided between the base 41 (second base region 41b) and the second conductive member 22. For example, the distance along the Z-axis direction between the second base region 41b and the second resistance member 12 is shorter than the distance along the Z-axis direction between the second base region 41b and the second conductive member 22.

In the embodiment, the processor 70 may include a current source. The processor 70 may include a voltage source. The current supplied by the current source or voltage source is provided to the sensing element, One current flows through the conductive member. Another current may be supplied to the resistance member and used to detect a value corresponding to the resistance of the resistance member.

The embodiments may include following configurations (for example, technical proposals).

Configuration 1

A sensor, comprising:
  a base including a first base region and a second base region,
  a first detection element portion provided at the first base region, the first detection element portion including a first detection element, the first detection element including a first resistance member and a first conductive member, the first resistance member including a first resistance portion and a first resistance other portion, the first conductive member including a first conductive portion and a first conductive other portion;
  a second detection element portion provided at the second base region, the second detection element portion including a second detection element, the second detection element including a second resistance member and a second conductive member, the second resistance member including a second resistance portion and a second resistance other portion, the second conductive member including a second conductive portion and a second conductive other portion;
  a first resistor terminal electrically connected with the first resistance portion;
  a second resistor terminal electrically connected with the first resistance other portion and the second resistance portion;
  a third resistor terminal electrically connected with the second resistance other portion;
  a first conductive terminal electrically connected with the first conductive portion; and
  a second conductive terminal electrically connected with the first conductive other portion.

Configuration 2

The sensor according to Configuration 1, further comprising a connecting conductive member provided on the base,
  the connecting conductive member electrically connecting the first resistance other portion and the second resistance portion.

Configuration 3

The sensor according to Configuration 1 or 2, further comprising a processor electrically connected with the first resistor terminal, the second resistor terminal, the third resistor terminal, the first conductive terminal, and the second conductive terminal,
  the processor being configured to perform a first operation of supplying a first current between the first conductive terminal and the second conductive terminal to raise the temperature of the first detection element,
  in the first operation, the processor being configured to output a signal corresponding to a first ratio of a first electric resistance between the first resistor terminal and the second resistor terminal to a second electric resistance between the second resistor terminal and the third resistor terminal.

Configuration 4

A sensor, comprising:
a base including a first base region and a second base region,
a first detection element portion provided at the first base region, the first detection element portion including a first detection element, the first detection element including a first resistance member and a first conductive member, the first resistance member including a first resistance portion and a first resistance other portion, the first conductive member including a first conductive portion and a first conductive other portion;
a second detection element portion provided at the second base region, the second detection element portion including a second detection element, the second detection element including a second resistance member and a second conductive member, the second resistance member including a second resistance portion and a second resistance other portion, the second conductive member including a second conductive portion and a second conductive other portion;
a first resistor terminal electrically connected with the first resistance portion;
a second resistor terminal electrically connected with the first resistance other portion;
a third resistor terminal electrically connected with the second resistance other portion;
a fourth resistor terminal electrically connected with the second resistance portion;
a first conductive terminal electrically connected with the first conductive portion; and
a second conductive terminal electrically connected with the first conductive other portion.

Configuration 5

The sensor according to Configuration 4, further comprising a processor electrically connected with the first resistor terminal, the second resistor terminal, the third resistor terminal, the fourth resistor terminal, the first conductive terminal, and the second conductive terminal,
the processor being configured to perform a first operation of supplying a first current between the first conductive terminal and the second conductive terminal to raise the temperature of the first detection element,
in the first operation, the processor being configured to output a signal corresponding to a first ratio of a first electric resistance between the first resistor terminal and the second resistor terminal to a second electric resistance between the third resistor terminal and the fourth resistor terminal.

Configuration 6

The sensor according to Configuration 3 or 5, wherein the first ratio changes according to a concentration of a first element included in an atmosphere around the first detection element and the second detection element.

Configuration 7

The sensor according to Configuration 3 or 5, wherein the first electric resistance of the first detection element when the temperature rises changes according to a concentration of a first element included in the atmosphere around the first detection element.

Configuration 8

The sensor according to Configuration 6 or 7, wherein the first element includes at least one selected from the group consisting of hydrogen, helium, carbon dioxide, methane and sulfur hexafluoride.

Configuration 9

The sensor according to one of Configuration 5-8, further comprising:
a third conductive terminal electrically connected with the second conductive portion; and
a fourth conductive terminal electrically connected with the second conductive other portion,
the processor is configured to perform a second operation switching from the first operation, the second operation including supplying a second current between the third conductive terminal and the fourth conductive terminal to raise a temperature of the second detection element,
in the second operation, the processor is configured to output a signal corresponding to a second ratio of a third electric resistance between the first resistor terminal and the second resistor terminal to a fourth electric resistance between the second resistor terminal and the third resistor terminal.

Configuration 10

The sensor according to Configuration 9, wherein the processor is configured to output an average of the first ratio and the second ratio.

Configuration 11

The sensor according to one of Configurations 1-10, wherein at least one of the second conductive portion or the second conductive other portion has a floating potential or a fixed potential.

Configuration 12

The sensor according to one of Configurations 1-11, wherein the second conductive member is a dummy conductive member.

Configuration 13

The sensor according to one of Configurations 1-12, wherein
the first detection element portion further includes a first connection portion and a first support portion,
the first support portion is fixed to the base,
a part of the first connection portion is supported by the first support portion,
an other part of the first connection portion supports the first detection element to be apart from the first base region,
the second detection element portion further includes a second connection portion and a second support portion,
the second support portion is fixed to the base,
a part of the second connection portion is supported by the second support portion, and
an other part of the second connection portion supports the second detection element to be apart from the second base region.

Configuration 14

The sensor according to Configuration 13, wherein
a first gap is provided between the first base region and the first detection element, and
a second gap is provided between the second base region and the second detection element.

Configuration 15

The sensor according to Configuration 13 or 14, wherein
the first detection element portion further includes a first other connection portion and a first other support portion,
the first other support portion is fixed to the base, a part of the first other connection portion is supported by the first other support portion,
an other part of the first other connection portion supports the first detection element to be apart from the first base region,
the second detection element portion further includes a second other connection portion and a second other support portion,
the second other support portion is fixed to the base,
a part of the second other connection portion is supported by the second other support portion,
an other part of the second other connection portion supports the second detection element to be apart from the second base region,
at least a part of the first detection element is located between the first connection portion and the first other connection portion, and
at least a part of the second detection element is located between the second connection portion and the second other connection portion.

Configuration 16

The sensor according to Configuration 15, wherein
the first detection element portion further includes a first conductive layer,
at least a part of the first conductive layer is provided at the first support portion,
a current flowing between the first resistor terminal and the first resistance portion flows through the first conductive layer,
the second detection element portion further includes a second conductive layer,
at least a part of the second conductive layer is provided at the second support portion, and
a current flowing between the second resistor terminal and the second resistance portion flows through the second conductive layer.

Configuration 17

The sensor according to Configuration 16, wherein the first detection element portion further includes a third conductive layer,
at least a part of the third conductive layer is provided at the first support portion, and
a first current flowing between the first conductive terminal and the first conductive portion flows through the third conductive layer.

Configuration 18

The sensor according to Configuration 17, wherein
the second detection element portion further includes a fourth conductive layer,
at least a part of the fourth conductive layer is provided at the second support portion, and
the fourth conductive layer is electrically connected with the second conductive portion.

Configuration 19

The sensor according to Configuration 16, wherein
the first detection element portion further includes a third connection portion, a third support portion, and a third conductive layer,
the third support portion is fixed to the base,
a part of the third connection portion is supported by the third support portion,
an other part of the third connection portion supports the first detection element to be apart from the first base region.
at least a part of the third conductive layer is provided at the third support portion, and
a first current flowing between the first conductive terminal and the first conductive portion flows through the third conductive layer.

Configuration 20

The sensor according to Configuration 19, wherein
the second detection element portion further includes a fourth connection portion, a fourth support portion, and a fourth conductive layer,
the fourth support portion is fixed to the base,
a part of the fourth connection portion is supported by the fourth support portion,
an other part of the fourth connection portion supports the second detection element to be apart from the second base region,
at least a part of the fourth conductive layer is provided at the fourth support portion, and
the fourth conductive layer is electrically connected with the second conductive portion.

According to the embodiments, it is possible to provide a sensor whose characteristics can be improved.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as base, detection element portion, processor, etc., from known art, Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a base including a first base region and a second base region,
a first detection element portion provided at the first base region, the first detection element portion including a first detection element, the first detection element including a first resistance member and a first conductive member, the first resistance member including a first resistance portion and a first resistance other portion, the first conductive member including a first conductive portion and a first conductive other portion;

a second detection element portion provided at the second base region, the second detection element portion including a second detection element, the second detection element including a second resistance member and a second conductive member, the second resistance member including a second resistance portion and a second resistance other portion, the second conductive member including a second conductive portion and a second conductive other portion;

a first resistor terminal electrically connected with the first resistance portion;

a second resistor terminal electrically connected with the first resistance other portion and the second resistance portion;

a third resistor terminal electrically connected with the second resistance other portion;

a first conductive terminal electrically connected with the first conductive portion; and a second conductive terminal electrically connected with the first conductive other portion.

2. The sensor according to claim 1, further comprising a connecting conductive member provided on the base, the connecting conductive member electrically connecting the first resistance other portion and the second resistance portion.

3. The sensor according to claim 1, further comprising a processor electrically connected with the first resistor terminal, the second resistor terminal, the third resistor terminal, the first conductive terminal, and the second conductive terminal, the processor being configured to perform a first operation of supplying a first current between the first conductive terminal and the second conductive terminal to raise the temperature of the first detection element, in the first operation, the processor being configured to output a signal corresponding to a first ratio of a first electric resistance between the first resistor terminal and the second resistor terminal to a second electric resistance between the second resistor terminal and the third resistor terminal.

4. A sensor, comprising:
a base including a first base region and a second base region, a first detection element portion provided at the first base region, the first detection element portion including a first detection element, the first detection element including a first resistance member and a first conductive member, the first resistance member including a first resistance portion and a first resistance other portion, the first conductive member including a first conductive portion and a first conductive other portion;

a second detection element portion provided at the second base region, the second detection element portion including a second detection element, the second detection element including a second resistance member and a second conductive member, the second resistance member including a second resistance portion and a second resistance other portion, the second conductive member including a second conductive portion and a second conductive other portion;

a first resistor terminal electrically connected with the first resistance portion;

a second resistor terminal electrically connected with the first resistance other portion;

a third resistor terminal electrically connected with the second resistance other portion;

a fourth resistor terminal electrically connected with the second resistance portion;

a first conductive terminal electrically connected with the first conductive portion; and a second conductive terminal electrically connected with the first conductive other portion.

5. The sensor according to claim 4, further comprising a processor electrically connected with the first resistor terminal, the second resistor terminal, the third resistor terminal, the fourth resistor terminal, the first conductive terminal, and the second conductive terminal, the processor being configured to perform a first operation of supplying a first current between the first conductive terminal and the second conductive terminal to raise the temperature of the first detection element, in the first operation, the processor being configured to output a signal corresponding to a first ratio of a first electric resistance between the first resistor terminal and the second resistor terminal to a second electric resistance between the third resistor terminal and the fourth resistor terminal.

6. The sensor according to claim 3, wherein the first ratio changes according to a concentration of a first element included in an atmosphere around the first detection element and the second detection element.

7. The sensor according to claim 3, wherein the first electric resistance of the first detection element when the temperature rises changes according to a concentration of a first element included in the atmosphere around the first detection element.

8. The sensor according to claim 6, wherein the first element includes at least one selected from the group consisting of hydrogen, helium, carbon dioxide, methane and sulfur hexafluoride.

9. The sensor according to claim 5, further comprising:
a third conductive terminal electrically connected with the second conductive portion; and
a fourth conductive terminal electrically connected with the second conductive other portion,
the processor is configured to perform a second operation switching from the first operation, the second operation including supplying a second current between the third conductive terminal and the fourth conductive terminal to raise a temperature of the second detection element,
in the second operation, the processor s configured to output a signal corresponding to a second ratio of a third electric resistance between the first resistor terminal and the second resistor terminal to a fourth electric resistance between the second resistor terminal and the third resistor terminal.

10. The sensor according to claim 9, wherein the processor is configured to output an average of the first ratio and the second ratio.

11. The sensor according to claim 1, wherein at least one of the second conductive portion or the second conductive other portion has a floating potential or a fixed potential.

12. The sensor according to claim 1, wherein the second conductive member is a dummy conductive member.

13. The sensor according to claim 1, wherein
the first detection element portion further includes a first connection portion and a first support portion,
the first support portion is fixed to the base,
a part of the first connection portion is supported by the first support portion,
an other part of the first connection portion supports the first detection element to be apart from the first base region, the second detection element portion further includes a second connection portion and a second support portion, the second support portion is fixed to the base, a part of the second connection portion is supported by the second support portion, and an other part of the second connection portion supports the second detection element to be apart from the second base region.

14. The sensor according to claim 13, wherein a first gap is provided between the first base region and the first detection element, and a second gap is provided between the second base region and the second detection element.

15. The sensor according to claim 13, wherein the first detection element portion further includes a first other connection portion and a first other support portion, the first other support portion is fixed to the base, a part of the first other connection portion is supported by the first other support portion, an other part of the first other connection portion supports the first detection element to be apart from the first base region, the second detection element portion further includes a second other connection portion and a second other support portion, the second other support portion is fixed to the base, a part of the second other connection portion is supported by the second other support portion, an other part of the second other connection portion supports the second detection element to be apart from the second base region, at least a part of the first detection element is located between the first connection portion and the first other connection portion, and at least a part of the second detection element is located between the second connection portion and the second other connection portion.

16. The sensor according to claim 15, wherein the first detection element portion further includes a first conductive layer, at least a part of the first conductive layer is provided at the first support portion, a current flowing between the first resistor terminal and the first resistance portion flows through the first conductive layer, the second detection element portion further includes a second conductive layer, at least a part of the second conductive layer is provided at the second support portion, and a current flowing between the second resistor terminal and the second resistance portion flows through the second conductive layer.

17. The sensor according to claim 16, wherein the first detection element portion further includes a third conductive layer, at least a part of the third conductive layer is provided at the first support portion, and a first current flowing between the first conductive terminal and the first conductive portion flows through the third conductive layer.

18. The sensor according to claim 17, wherein the second detection element portion further includes a fourth conductive layer, at least a part of the fourth conductive layer is provided at the second support portion, and the fourth conductive layer is electrically connected with the second conductive portion.

19. The sensor according to claim 16, wherein the first detection element portion further includes a third connection portion, a third support portion, and a third conductive layer, the third support portion is fixed to the base, a part of the third connection portion is supported by the third support portion, an other part of the third connection portion supports the first detection element to be apart from the first base region, at least a part of the third conductive layer is provided at the third support portion, and a first current flowing between the first conductive terminal and the first conductive portion flows through the third conductive layer.

20. The sensor according to claim 19, wherein the second detection element portion further includes a fourth connection portion, a fourth support portion, and a fourth conductive layer, the fourth support portion is fixed to the base, a part of the fourth connection portion is supported by the fourth support portion, an other part of the fourth connection portion supports the second detection element to be apart from the second base region, at least a part of the fourth conductive layer is provided at the fourth support portion, and the fourth conductive layer is electrically connected with the second conductive portion.

* * * * *